United States Patent [19]

Berger

[11] Patent Number: 4,574,084

[45] Date of Patent: Mar. 4, 1986

[54] PROCESS FOR THE PREPARATION OF A MODIFIED AQUEOUS CHLORITE SOLUTION, THE SOLUTION PREPARED BY THIS PROCESS AND THE USE THEREOF

[76] Inventor: Peter Berger, Rathausstrasse 44,, 6900 Heidelberg, Fed. Rep. of Germany

[21] Appl. No.: 668,273

[22] PCT Filed: Feb. 2, 1984

[86] PCT No.: PCT/EP84/00046

§ 371 Date: Oct. 24, 1984

§ 102(e) Date: Oct. 24, 1984

[87] PCT Pub. No.: WO84/03274

PCT Pub. Date: Aug. 30, 1984

[30] Foreign Application Priority Data

Feb. 25, 1983 [DE] Fed. Rep. of Germany ....... 3306753
Mar. 3, 1983 [DE] Fed. Rep. of Germany ..... 33075697

[51] Int. Cl.$^4$ .................... A61K 33/20; A61K 33/40; A61K 33/42
[52] U.S. Cl. .................................. 424/128; 424/130; 424/149; 424/164
[58] Field of Search ....................... 424/130, 128, 149

[56] References Cited

U.S. PATENT DOCUMENTS 2,358,866  9/1944  MacMahan ......................... 252/187
3,271,242  9/1966  McNicholas et al. .............. 424/130
4,296,103 10/1981  Laso .................................... 424/130

Primary Examiner—Leonard Schenkman
Attorney, Agent, or Firm—Darby & Darby

[57] ABSTRACT

A process for the preparation of a stabilized, modified, aqueous chlorite solution with a peroxy compound content is described. A weak, acid, aqueous solution of a peroxy compound substantially stable therein is provided and into this solution is metered an aqueous solution of a chlorite until the pH-value of 7 is exceeded, accompanied by the formation of a greenish solution. The peroxy compounds can in particular be peroxy sulphates, percarbonates and perborates of alkali metal or alkaline earth metals, as well as hydrogen peroxide. The chlorite solutions obtainable according to the above process are stable over a long period and have a high oxidative activity, particularly when used as a biocide. The biocidal action can be used with particular advantage in water treatment and in the external treatment of skin diseases.

20 Claims, No Drawings

PROCESS FOR THE PREPARATION OF A MODIFIED AQUEOUS CHLORITE SOLUTION, THE SOLUTION PREPARED BY THIS PROCESS AND THE USE THEREOF

TECHNICAL FIELD

The invention relates to a process for the preparation of a stabilized, modified, aqueous chlorite solution with a content of a peroxy compound, the chlorite solution obtained by this process and the multiple possible uses thereof as a biocide.

BASIC PRIOR ART

Modified, aqueous, chlorite solutions, particularly aqueous sodium chlorite solutions stabilized by means of peroxy compounds have a large number of different uses in technology and in other fields, such as e.g. for oxidative purposes. Such solutions are inter alia used for the treatment of water to be used as drinking water, as well as swimming pool water and water for industrial use for disinfection purposes.

The stability thereof is not adequate. Therefore, numerous attempts have been made to obviate this shortcoming. It is generally known to use alkaline stabilizing agents, such as e.g. sodium carbonate, as well as hydrogen peroxide and inorganic compounds derived therefrom, such as e.g. perborates.

It is also known that aqueous chlorite solutions, in which chlorine dioxide is in equilibrium with chloric acid in the acid range, can be stabilized by means of pyridine (cf Holleman/Wiberg "Lehrbuch der anorganischen Chemie", 47–56 edition, 1960, p. 127). The stabilized chlorite solution prepared in this way is also not sufficiently stable. Moreover, pyridine-stabilized chlorite solutions cannot be used in systems, where an additional loading with an organic substance is to be avoided, such as e.g. in drinking water and swimming pool water treatment. In addition, pyridine is a carcinogenic substance.

Stabilized and even unstabilized chlorite solutions play a particular part in the treatment of swimming pool water. Conventional, also stabilized chlorite solutions, must undergo an acid reaction course at a pH-value $\leq 3$ in such a "chlorine/chlorine dioxide process". For this purpose, it is necessary to use special equipment, which is not directly integrated into the water cycle. This applies both to the acid process and to the hypochlorous acid process, which are subordinate to the aforementioned chlorine/chlorine dioxide process. If sodium chlorite and hydrochloric acid are used, then sodium chloride and chlorine dioxide are formed therefrom according to this so-called hydrochloric acid process at the aforementioned pH-value. For the purposes of this reaction, reaction towers with Raschig rings are recommended in a size guaranteeing a corresponding reaction time, in order to obtain a very high conversion rate. This is also intended to ensure that on introducing the reaction product, the residual chlorite content in the swimming pool water is as low as possible, particularly max. 0.1 mg/l. To prevent a redisproportioning to chlorite-chlorate, the chlorine to chlorine dioxide ratio in the swimming pool water is fixed at 10:1. In the aforementioned hypochlorous acid process, the reactions take place in the following way. For example, a sodium chlorite solution and chlorine are metered into a water tank upstream of the water disinfection process. A reaction then takes place at a pH-value of $\leq 3$, in which hypochlorous acid is formed as an intermediate stage and finally chlorine dioxide. The thus prepared solution is then metered into the pool water as required.

In both the aforementioned processes (acid process and hypochlorous acid process), high expenditure on equipment is necessary and it must also be constantly ensured that in the acid process the hydrochloric acid supply is absolutely ensured and in the hypochlorous acid process that the chlorine supply is absolutely ensured, in order to avoid a disadvantageous metering of unreacted chlorite into the pool water. However, as occasionally deficiencies cannot be reliably prevented, this always constitutes a risk for the bather. In addition, the accidental mixing of commercial chlorite solutions with acids leads to explosive phenomena.

DISCLOSURE OF THE INVENTION

The problem of the invention is therefore to so improve the aforementioned processes, that a more stable process product can be prepared, which can be safely and more reliably used for the treatment of water, particularly swimming pool water and which also has further uses.

According to the invention, this problem is solved in that a weak acid aqueous solution of a peroxy compound which is substantially stable therein is provided and into this solution is metered an aqueous solution of a chlorite until the pH-value of 7 is exceeded, accompanied by the formation of a greenish solution.

Thus, according to the invention, therefore for stabilizing the chlorite in the aqueous solution, peroxy compounds are used which stabilize on a long-term basis the oxidation system based on the chlorite while retaining the sought oxidative activity. The term "peroxy compounds" is to be understood in its broadest sense and covers hydrogen peroxide ($H_2O_2$), as well as hydrogen peroxide derivatives, particularly peroxy compounds (preferably in the form of inorganic compounds), which contain the ion $O_2^{2-}$ as a ligand, or in which —O— is replaced by —O—O—, peroxides and peracids. The peroxy compounds more particularly include inorganic peroxy acids, together with their salts. Preference is given to perborates, percarbonates and persulphates. The peracids usable according to the invention include not only the aforementioned peroxy acids, but also oxy acids of the perchloric acid type, including their salts. The said salts are preferably alkali metal and alkaline earth salts, with particular reference to the corresponding sodium, potassium and calcium compounds. The stabilization by peroxides preferably takes place by barium or sodium peroxide.

For the case where the stabilized, modified chlorite solution is used in systems where additionally introduced, organic substances are unobjectionable, the aforementioned peroxy compounds can also be organic. Within the scope of the given teaching, the expert will be able to find further stabilizing peroxy compounds, which are suitable for the purposes of the invention. One will also be able to readily determine the appropriate concentration of the stabilizing peroxy compound. It is surprising that preferably relatively small peroxy compound concentrations are adequate for the purposes of the invention and when using the stabilized products, particularly favorable effects are obtained. This more particularly applies with a 0.001 to 0.01 molar concentration of the peroxy compound in the greenish finished solution. It is possible to drop below or rise above this range, as a function of the particular aqueous system, the selected starting materials and the field of use, e.g. by a decimal point. With respect to the objectives of the invention, higher concentrations regularly lead to no advantages and frequently exclude the sought effects, or do not lead to them being obtained in the sought manner. Moreover, the small stabilizing peroxy compound quantity required by the invention means that there is substantially no cost increase.

In the process according to the invention, a suitable stabilizing peroxy compound is converted into a weak acid solution. This solution preferably has a pH-value of $\leq 3$, which $\leq 1$ is particularly advantageous. In the case of the latter value, there is not only an optimum performance of the process, but a particularly well-stabilized product is obtained. Acidification can take place by means of mineral acids such as hydrochloric acid, sulphuric acid, etc, but also by adding hydrogen compounds, i.e. acid, organic salts, particularly alkali metal or alkaline earth salts, or in the form of a combination of the above compounds. Preference is given to sodium, potassium and calcium salts, particularly in the form of their hydrogen sulphates.

When selecting the acidifying compounds, account must also be taken of the subsequent use of the product according to the invention. It is generally particularly advantageous for acidification to take place with sulphuric acid. In connection with the uses of the product according to the invention to be described hereinafter, it has been found that if there are sulphate ions, the effects are particularly favorable. For example, it is possible to proceed in such a way that a sulphate is added and that acidification takes place with another acid. Fundamentally, it is possible to use hydrochloric acid. However, compared with the use of sulphuric acid, this leads to a certain disadvantage that, despite the described interaction with chlorite, excessive chloride quantities prematurely lead to the formation of chlorine dioxide and not only when this is required, and this disturbs the desired equilibrium system, accompanied by gassing out and consequently to chlorine dioxide removal. This leads to an undesired weakening of the system in the sense of the invention.

Into the above-described, weak acid aqueous solution of the peroxy compound is metered an aqueous chlorite solution and its concentration is not decisive. Thus, it can in particular be a commercial aqueous alkali metal and/or alkaline earth chlorite solution, particularly a sodium and/or calcium chlorite solution. The pH-value of the commercial alkali metal chlorite solution is generally above 12. Solutions of this type regularly contain approximately 300 g/l. However, it is obviously possible to drop below this value. As according to the invention, regularly a strong concentrated, stabilized and modified chlorite solution is sought, it is obvious to use a strong, concentration chlorite solution as the starting material. The metering in of the starting chlorite solution preferably takes place with stirring until the original partly gassing, dark brown solution has assumed a greenish yellow or greenish shade. This is generally the case when the pH-value is above 7. Preference is given to a pH-value of approximately 7 to 8 and particularly 7.5 to 8.

It has surprisingly been found that in the process according to the invention, the peroxy compound quantity can be drastically reduced if a water-soluble phosphate, e.g. sodium metapolyphosphate is incorporated in a small quantity into the finished solution.

In the case of the process according to the invention, an excessive reaction in the form of explosive phenomena can occur if the aqueous starting solutions used only have a limited carbonate hardness, or when demineralized water is involved. In such cases, it is advisable to work under an inert gas atmosphere. Preferably, prior to the metering in of the chlorite solution, a generally adequate small quantity of a hydrogen carbonate, e.g. sodium hydrogen carbonate, is metered into the acid aqueous solution. In the case of aqueous starting solutions with an average or high carbonate hardness, such a measure is not generally necessary, because a type of inert gas layer of carbon dioxide is formed between the slightly gassing chlorine dioxide and the air. Thus, no explosive air/chlorine dioxide mixture can form. In the case of an air to chlorine dioxide ratio of approximately 10:1, such a mixture tends towards an explosive decomposition of the chlorine dioxide into chlorine and oxygen.

The stabilized modified chlorite solution according to the invention has an extremely favorable storage period of several months, without there being any significant reduction to the desired oxidative action. After some time, there is a yellow-brown coloring as a result of the proportionately released chlorine dioxide, but this does not significantly impair the desired activity. If the released chlorine dioxide proportion is removed from the aqueous solution, e.g. by extraction by shaking, then after a short time the desired greenish coloring of the clear aqueous solution reappears. This means that in the sense of an equilibrium reaction, the chlorite solution always re-forms chlorine dioxide during the removal thereof. This occurs with high dilution, also e.g. when the chlorine dioxide formed has used up its oxidative action through the influence of reducing substances, particularly organic substances.

Unlike in the conventional prior art chlorite solutions, in the stabilized modified chlorite solution according to the present invention, there is a positive redox potential between approximately 450 and 500 mV, as a function of the light action. It is important for the subsequent action, as well as for the action ranges described hereinafter that a stabilizing effect is obtained with a minimum, controllable quantity of a peroxy compound. As the stabilizing action of peroxy compounds with respect to chlorine dioxide or chlorite solutions is highly pH-dependent according to the known procedure, a relatively large amount of peroxy compound must be added to an acid chloride dioxide solution to be stabilized. This also applies for stabilization in the alkaline range. In this case, large peroxy compound excesses must be added, because this compound decomposes strongly in the alkaline range. Following pH-reduction, it is no longer possible to establish what peroxy proportions are still present in the finished solution. In principle, larger peroxy compound proportions lead to an unacceptable interference to the subsequent use of the two last-described, prior art chlorite solutions in the aforementioned use ranges. In addition, a chlorite solution in specific use ranges should as far as possible be roughly pH-neutral which, unlike in the case of the chlorite solution according to the invention, does not apply for the aforementioned prior art solutions. The technological background will be made even clearer during the following comments with respect to the prior art.

For example, the following procedure is used in the process according to the invention. A very small quantity of a peroxy compound is added to an acid (particularly sulphuric acid) solution, whose pH-value is preferably $\leq 1$, so that there is an approximately 0.0022 mol peroxy compound concentration in the finished chlorite solution. This finished solution contains approximately 100 g of chlorine dioxide per liter. In order to stabilize such a chlorine dioxide quantity with minimum amounts of peroxy compounds in the pH-range of 7 to 8, the following procedure is adopted. Approximately 6 kg of a bubbled sodium hydrogen sulphate is incorporated, accompanied by stirring, into approximately 200 liters of tap water with a carbonate hardness of 18. Approximately 100 ml of a 30% $H_2O_2$ solution is added to the aforementioned solution. After stirring for roughly 10 minutes, 200 liters of an approximately 30% sodium chlorite solution is added to the aforementioned solution over a period of roughly 10 minutes until the neutral point is reached. In the still strong acid phase, the small peroxy compound quantity is adequate to keep the still small chlorine dioxide proportion stable. As with rising pH-value, the stabilizing nature of the peroxy compound with respect to chlorine dioxide increases, the processes take place in accordance with a self-controlling equivalent. Possibly a complex compound of chlorine dioxide forms where, unlike in other known processes, the peroxy compound does not act in the chemical reaction mechanism (such as e.g. in accordance with the equation $2\ ClO_2 + 2\ HO^- + H_2O_2 \rightarrow 2\ ClO_2^- + 2\ H_2O + O_2$). On reaching a pH-value of approximately 7, the previously dark brown solution changes to lime green and has an oxidation potential of approximately 300 mV. If this solution is exposed to direct or indirect daylight for 24 hours, after a certain time a so-called kick reaction occurs and the solution assumes a golden yellow color. This is linked with a potential jump to approximately +450 to 550 mV.

If the solution prepared in the aforementioned manner is now treated with carbon tetrachloride, the free chlorine dioxide proportion is consequently extracted by shaking, which means that the free chlorine dioxide passes into the carbon tetrachloride phase, accompanied by yellow coloring, whilst the aqueous phase is pale. However, after a short time, it is found that chlorine dioxide has been reintroduced into the remaining aqueous phase (yellow coloring). This procedure can be repeated until the aqueous phase is exhausted. If the stabilized chlorite solution according to the invention is added to warm water, there is a slight ozone odour, apart from the typical chlorine-like odor.

If the solution according to the invention is highly diluted with water, then the equilibrium thereof is displaced in the direction of the chlorine dioxide, which still applies in the pH-range of approximately 7 to 8.5.

If the stabilized, modified chlorite solution according to the invention is used, then the desired action of the neutral or weak alkaline solution by acidification or accompanied by the action of a random reactant, e.g. chlorine, accompanied by the release of chlorine dioxide, takes place in such a way that under normal conditions a yellowish-reddish gas is provided. Due to the presence of chlorine, particularly with an elevated chloride proportion, or mineral acids in a treated aqueous system, the chlorine dioxide formation reaction takes place in privileged manner compared with the undesired chlorate reaction. The desired reaction sequence is not disturbed, even on adding strong mineral acids in high concentration, which is not the case with the known chlorite solutions. Under the action of strong mineral acids, these known solutions still exhibit the aforementioned explosive phenomena.

There are also cases where the chlorite solution according to the invention is subject to destabilization, in that the system to be treated contains a reactant for the peroxy compound present in small quantities and reduces the latter and consequently eliminates the stabilization of the chlorite solution. Such a reactant can e.g. be the peroxidases and catalases present in germ cells, i.e. enzymes of the animal and vegetable metabolism belonging to the group of peroxidoreductases. The action thereof leads to the spontaneous release of chlorine dioxide. As a result, the stabilized, modified chlorite solution gives high selectivity when used biocidally in small quantities.

The chlorite solution according to the invention, particuarly in the form of a sodium chlorite solution can be used particularly advantageously in water treatment. This mainly refers to the treatment of drinking water, water for industrial use and swimming pool water for disinfecting purposes. This disinfection preferably takes place accompanied by the simultaneous use of chlorine, so that chlorine dioxide, which is highly effective for disinfection purposes, is formed. For example, a sodium chlorite solution with approximately 300 g of sodium chlorite per liter is used for preparing the chlorite solution according to the invention. The finished solution generally contains 8 to 15% by weight of chlorine dioxide, the range 10 to 12% by weight being regularly particularly advantageous. It is also possible to add to this solution various other constituents, such as sodium chloride, sodium sulphate and sodium chlorate. The sodium chlorite solution according to the invention can be so adjusted by dilution, that it satisfies the KOK (coordination committee for swimming pool construction and operation) guidelines, which stipulate a residual chlorite content in swimming pool water of max. 0.3 mg/l of pool water. It then also satisfies the DIN draft 19643 of max. 0.1 mg/l. The above comment also applies to other chlorite solutions, such as other alkali metal and alkaline earth chlorite solutions.

The chlorite solution according to the invention is particularly advantageous in the treatment of swimming pool water, as will be described in greater detail hereinafter.

It is firstly stressed that the explosive phenomena referred to hereinbefore in connection with known processes are eliminated when the chlorite solution according to the invention is used. Even on mixing with concentrated sulphuric acid, an explosion cannot occur. Its particular suitability for the treatment or conditioning of swimming pool water has been proved by an expert opinion of the Gelsenkirchen Institute of Hygiene. In connection with an equivalence proof, it was found that the solution according to the invention behaves quite differently to commercial chlorite solutions or solutions stabilized in some other way. In the tests performed by the Institute of Hygiene, the solution according to the invention was metered by means of a fine metering pump via an inoculation point between the flocculation inoculation point and the filter directly into the pool water circuit (pH-value of 7.5). All the water samples taken revealed chlorine dioxide, but not the chlorite ($ClO^-_2$) to be avoided. It is also important in this connection that even very small amounts of peroxy compounds have a disturbing action in chlorinated pool water. With respect to strong oxidizing agents, such as chlorine, peroxides assume a reductive character. Thus, they considerably reduce the oxidation potential which, in swimming pool water, plays an important part for the germ killing rate. In many swimming pools the addition of disinfectant is automatically controlled via this parameter. In the case of an artificial change (reduction) of the oxidation potential, vast quantities of e.g. chlorine was passed uncontrolled into the pool water. This risk is largely eliminated by the use of the chlorite solution according to the invention. The small peroxy compound quantities introduced into the pool circuit are of an order of magnitude which can just be eliminated by e.g. finely divided metal impurities on the filter or peroxidases occurring in certain germs. As a result of the chlorine dioxide spontaneously selectively released in this way in contaminated filter material, additional phenomena occur which do not take place in conventional chlorine/chlorine dioxide processes.

The aforementioned equivalence proof revealed that the time between the necessary filter backwashes after differential pressure could be doubled or the pool water quantity required for backwashing could be reduced by half. It was also found that the filter treated with the solution according to the invention can discharge double the pollutant quantity in half the time. This is possibly due to a better flocculation of the organic/inorganic loading substances and to a prevention of the adhering over of the filter material. This permits an easier, faster discharge of the collected pollutant particle. The chlorite solution according to the invention also prevents strong contamination of highly loaded filters. Thus, in the specifically adjusted manner it acts as a filter aid. Its described use leads to considerable savings in fresh water, waste water, heating and treatment costs. The following occurred in connection with the Bockum/Hö vel, Hamm indoor swimming pool used for the equivalence proof. During the normal treatment, flocculation-filtering-chlorination, the necessary amount of fresh water per bather is 0.11 m$^3$. When using the chlorite solution according to the invention on average 0.03 m$^3$ of fresh water are required for each bather. Thus, the saving for each bather is 0.08 m$^3$.

Thus, the following statements can be made in connection with the use of the chlorite solution according to the invention for the treatment of swimming pool water. This solution can be directly added to the chlorinated swimming pool water, chlorine dioxide being directly formed in the pH-range of approximately 7 to 7.8. However, the treatment with the solution according to the invention preferably takes place between the flocculation and the filtering stages. There can e.g. be approximately 24 ml of a roughly 10% by weight chlorite solution for approximately 180 m$^3$ of circulated swimming pool water. The 100% conversion to chlorine dioxide takes place so rapidly that in the case of crude water-side metering, no chlorite but only chlorine dioxide could be detected on the pure waterside. The water quality obtained is superior to that of known processes (acid or hypochlorous acid processes). As shown, the treatment process operating with the agent according to the invention is very inexpensive.

The stabilized, modified chlorite solutions according to the invention also have further advantageous uses. Thus, it has been found that in particular dilute chlorite solutions according to the invention have excellent biocidal actions in the broadest sense. This more particularly applies to a dilute sodium chlorite solution, preferably with an approximately 0.1 to 0.5% by weight concentration. It can be used for hygienic, disinfecting personal hygiene, e.g. for foot care in swimming pools, saunas, etc, particularly in the treatment of perspiring feet. It is also very suitable in the case of externally treatable skin diseases and irritations, particularly skin eruptions, psoriasis, eczema, lupus, hymenomycetes or generally in inflammatory skin diseases, which are caused by bacteria and protozoa, viruses or fungi (candidamycosis, trichophytia, pityriasis, herpes, etc). The agent according to the invention and particularly the sodium chlorite solution can also be used for treating skin diseases in the throat or mouth, such as bleeding of the gums. Thus, these agents are a type of medicament. In addition, the chlorite solution according to the invention can be generally considered as a cosmetic, which can be added in small concentrations to the bath water when bathing. Certain of the aforementioned uses will be described in greater detail hereinafter.

In pharmaceutical fields, it has been found that the solution according to the invention is compatible with the skin to a high degree. It can even be supplied in concentrated form to the healthy skin, without allergic reactions being detected. The skin generally acts highly allergically to normal chlorite solutions of the same concentration. It was in fact found that a dilute chlorite solution according to the invention led to surprising improvements to allergies. In dilutions of the concentrated solution to water of 1:10, there were even found to be spectacular antimycotic actions. The chlorite solution according to the invention also proved to be effective in healing severe neurodermititis, which had in part persisted for some years. However, the solution must be highly diluted here, e.g. 20 to 30 ml per bath with a slow increase up to the limit of the compatibility of the particular patient.

A very surprising phenomenon occurs in the treatment of psoriasis, with baths every day or every two days (approximately 100 ml/bath, while excluding other additives) the scales were detached with roughly 80% of the patients after the first few baths and without any mechanical action and itching generally rapidly decreased. The raised skin parts became flatter and the dark red coloring turned pale pink. Following a generally occurring stagnation phase of approximately 2 to 3 months, the previously attached skin parts normalized. A function is possibly played during this treatment by the successive release of small ozone quantities during bathing (metabolism regulation via the large-area skin contact). Persistent perspiration odors were eliminated by bathing the body and feet. Other uses include mouthwashes with a 3% solution, which eliminates bleeding of the gums.

A further surprising action was found during the treatment of diabetic gangrene. In one case, a wound as wide as the thumb and about 7 cm long healed on bathing with a dilute sodium chlorite solution according to the invention (dilution with water in ratio 1:100) following treatment for about 8 weeks.

Finally, chlorite solutions according to the invention and preferably the sodium chlorite solution, can be used industrially, e.g. in combatting slime in water systems. This more particularly applies to the conservation of drinking water in various containers or tanks, particularly on ships. Such a solution can in such cases be used very effectively and without application problems. The drinking water treated with the solution according to the invention remained germ-free for several months in closed containers. With the ppm range quantities used, there was no deterioration to the taste of the water. There were also no toxicological objections.

The oxidizing effect of the chlorite solutions according to the invention can e.g. be used in wider technical fields, e.g. in the combination with mineral acids or chlorine. Thus, they can be used in the production of cellulose, the bleaching of oils, fats, waxes and leather and for disinfecting or deodorizing evil-smelling waste and sewage. A special application is the stagewise bleaching of pulp.

In summarizing, it can be stated that the stabilized, modified, aqueous chlorite solution according to the invention can be advantageously used wherever it is to lead to an oxidative action, particularly due to the formation of chlorine dioxides. This can be dead matter of organic, particularly reducing substances, as well as living organisms, such as microorganisms, fungi and the like. Thus, the chlorite solution according to the invention can be considered in the broadest sense as a biocidally active agent with absolute skin compatibility, i.e. it can be used as an insecticide, fungicide, herbicide, etc, where hitherto commercial sodium chlorite solutions have either proved unsuitable or have only had a limited success. A particular advantage of the chlorite solution according to the invention is that it generally permits a 100% conversion of the chlorite into chlorine dioxide in a wide pH-range, particularly also in an alkaline medium. Thus, the literature describes that chlorite solutions only lead to the desired 100% conversion rate to chlorine dioxide in a pH-range of $\leq 3$. In addition, the solution according to the invention can be very simply prepared, in that e.g. the acid solution (preferably with a pH-value $\leq 1$) is mixed with a concentrated, commercial chloride solution in a volume ratio of approximately 1:1 until a pH-value just above 7 is obtained.

The invention is further illustrated hereinafter by means of an example:

EXAMPLE 0.5 g of a 30% by weight hydrogen peroxide solution is added to 1 liter of water (carbonate hardness: 18°) with a pH-value of 0.5. 0.9 liters of a commercial sodium chlorite solution (approximately 300 g of sodium chlorite/liter) is added to this solution, accompanied by adequate stirring. The solution has a brown coloring and on exceeding the pH-value of 7 and following the stabilization reaction changes to a light, lime green color. A pH-value of approximately 7.5 is obtained in the solution, which gives a 100% conversion to chlorine dioxide when treating the water of an indoor swimming pool. Conversion takes place so quickly that on the pure water side, chlorite was never detected, although small amounts of chlorine dioxide were found. The water quality is significantly improved. The fresh water addition per bather can be reduced to 20%.

The aqueous solution prepared in the aforementioned manner, inter alia has an excellent action in the treatment of psoriasis and hymenomycetes when used in a 0.1 to 0.5% by weight concentration.

I claim:

1. A process for the preparation of a stabilized, modified, aqueous chlorite solution comprising the steps of:
providing an aqueous acid solution having a pH of less than about 3;
adding a peroxy compound to said aqueous acid solution; and
introducing an aqueous chlorite solution into the acid solution to which said peroxy compound has been added, until the pH of said acid solution exceeds 7 and the solution becomes a greenish color.

2. Process according to claim 1 wherein said peroxy compound is inorganic.

3. Process according to claim 1 wherein said inorganic peroxy compound is selected from the group consisting of alkali metal persulfates, percarbonates, perborates, peroxides, alkaline earth metal persulfates, percarbonates, perborates and peroxides.

4. Process according to claim 1 wherein said peroxy compound is hydrogen peroxide.

5. Process according to claim 1 wherein said peroxy compound is added to said aqueous acid solution to form a 0.001 to 0.01 molar concentration of said peroxy compound in said stabilized, modified, aqueous chlorite solution.

6. Process according to claim 1 wherein said aqueous acid solution has a pH of 1 or less.

7. Process according to claim 1 wherein said stabilized, modified, aqueous chlorite solution is prepared under an inert gas atmosphere.

8. Process according to claim 1 wherein said stabilized, modified, aqueous chlorite solution further comprises a water-soluble phosphate.

9. Process according to claim 8 wherein said water-soluble phosphate is sodium meta-polyphosphate.

10. A stabilized, modified, aqueous chlorite solution prepared by the steps comprising:
providing an aqueous acid solution having a pH of less than about 3;
adding a peroxy compound to said aqueous acid solution; and
introducing an aqueous chlorite solution into the acid solution to which said peroxy compound has been added, until the pH of said acid solution exceeds 7 and the solution becomes a greenish color.

11. The stabilized chlorite solution of claim 10 wherein said peroxy compound is inorganic.

12. The stabilized chlorite solution of claim 10 wherein said inorganic peroxy compound is selected from the group consisting of alkali metal persulfates, percarbonates, perborates, peroxides, alkaline earth metal persulfates, percarbonates, perborates and peroxides.

13. The stabilized chlorite solution of claim 10 wherein said peroxy compound is hydrogen peroxide.

14. The stabilized chlorite solution of claim 10 wherein said peroxy compound is added to said aqueous acid solution to form a 0.001 to 0.01 molar concentration of said peroxy compound in said stabilized, modified, aqueous chlorite solution.

15. The stabilized chlorite solution of claim 10 wherein said aqueous acid solution has a pH of 1 or less.

16. The stabilized chlorite solution of claim 10 wherein said stabilized, modified, aqueous chlorite solution is prepared under an inert gas atmosphere.

17. The stabilized chlorite solution of claim 10 wherein said stabilized, modified, aqueous chlorite solution contains a water-soluble phosphate.

18. The stabilized chlorite solution of claim 17 wherein said water-soluble phosphate is sodium meta-polyphosphate.

19. A method for treating a mammal having a skin disease or skin irritation which comprises topically administering to a mammal in need of such treatment an effective amount of a stabilized, modified, aqueous chlorite solution prepared by the steps including:

providing an aqueous acid solution having a pH of less than about 3;

adding a peroxy compound to said aqueous acid solution; and introducing an aqueous chlorite solution into the acid solution to which said peroxy compound has been added, until the pH of said acid solution exceeds 7 and the solution becomes a greenish color.

20. A method for the biocidal treatment of swimming pool water which comprises introducing to the water circuit of a swimming pool a stabilized, modified, a aqueous chlorite solution prepared by the steps including:

providing an aqueous acid solution having a pH of less than about 3;

adding a peroxy compound to said aqueous acid solution; and introducing an aqueous chlorite solution into the acid solution to which said peroxy compound has been added, until the pH of said acid solution exceeds 7 and the solution becomes a greenish color.

* * * * *